United States Patent [19]

Pettit

[11] Patent Number: 4,486,414
[45] Date of Patent: Dec. 4, 1984

[54] DOLASTATINS A AND B CELL GROWTH INHIBITORY SUBSTANCES

[75] Inventor: George R. Pettit, Paradise Valley, Ariz.

[73] Assignee: Arizona Board of Reagents, Tempe, Ariz.

[21] Appl. No.: 477,045

[22] Filed: Mar. 21, 1983

[51] Int. Cl.$^3$ ............... A61K 37/02; C07G 7/00
[52] U.S. Cl. ............... 424/177; 260/112 R; 424/95
[58] Field of Search ............... 424/95, 177; 260/112 R

[56] References Cited

U.S. PATENT DOCUMENTS 4,414,205  11/1983  Pettit ................... 424/177

OTHER PUBLICATIONS

Watson-Ph.D. Dissert (Abs.) Univ. Microfilms, Inc. Ann Arbor, Mi, (1969).
Engel-Zool, Med. Leiden, vol. 24, (1945), pp. 197–239.

Primary Examiner—Sam Rosen
Attorney, Agent, or Firm—Lawrence T. Welch; Roman Saliwanchik

[57] ABSTRACT

Potent cell growth inhibitory substances have been obtained from the Indian Ocean sea hare Dolabella. These substances have been given the names dolastatin A and dolastatin B. These compounds are characterized by physical and chemical parameters.

7 Claims, 2 Drawing Figures

FIGURE I
Fractionation of F005 plus F006

```
     F005              F006
    (14 g)            (10 g)
       |_____|
                |
                |  Silica gel
                |  Hexane/EtOAc → EtOAc/MeOH/H₂O
              6.385 g
   ED₅₀ = 0.14
                |  Silica gel
                |  CH₂Cl₂/MeOH/H₂O
              1.135 g
   ED₅₀ = 8.6 x 10⁻³
                |  Sephadex LH-60,
                |  hexane/CH₂Cl₂/MeOH, 10:10:1
              F052, 120 mg
   ED₅₀ <10⁻³; T/C 155 (2.25 mg)
                |  HPLC, C-18 bonded silica gel,
                |  MeOH/H₂O (10/90 → 95/5)
              42 mg
                |  HPLC, silica gel
                |  1. EtOAc/EtOH (100/0 → 4/6)
                |  2. CH₂Cl₂/MeOH/H₂O
                |     (99:1:0.05 → 75:25:3)
              F091, 7.7 mg
   ED₅₀ < 10⁻⁴; T/C 140 (0.3 mg)
                |  1. HPLC, silica gel,
                |     CH₂Cl₂/MeOH/H₂O, 97:3:0.2
                |  2. Prep. TLC, silica gel,
                |     CH₂Cl₂:MeOH, H₂O,
                |     90:10:0.8
        _____|_____
       |                 |
      K095              K094
   Dolastatin A      Dolastatin B
     (3.5 mg)          (1.5 mg)
 ED₅₀: 1.8 x 10⁻⁸     > 10⁻⁴
```

- $ED_{50} = 0.14$
- $ED_{50} = 8.6 \times 10^{-3}$
- $ED_{50} < 10^{-3}$; T/C 155 (2.25 mg)
- $ED_{50} < 10^{-4}$; T/C 140 (0.3 mg)
- $ED_{50}: 1.8 \times 10^{-8}$
- $> 10^{-4}$

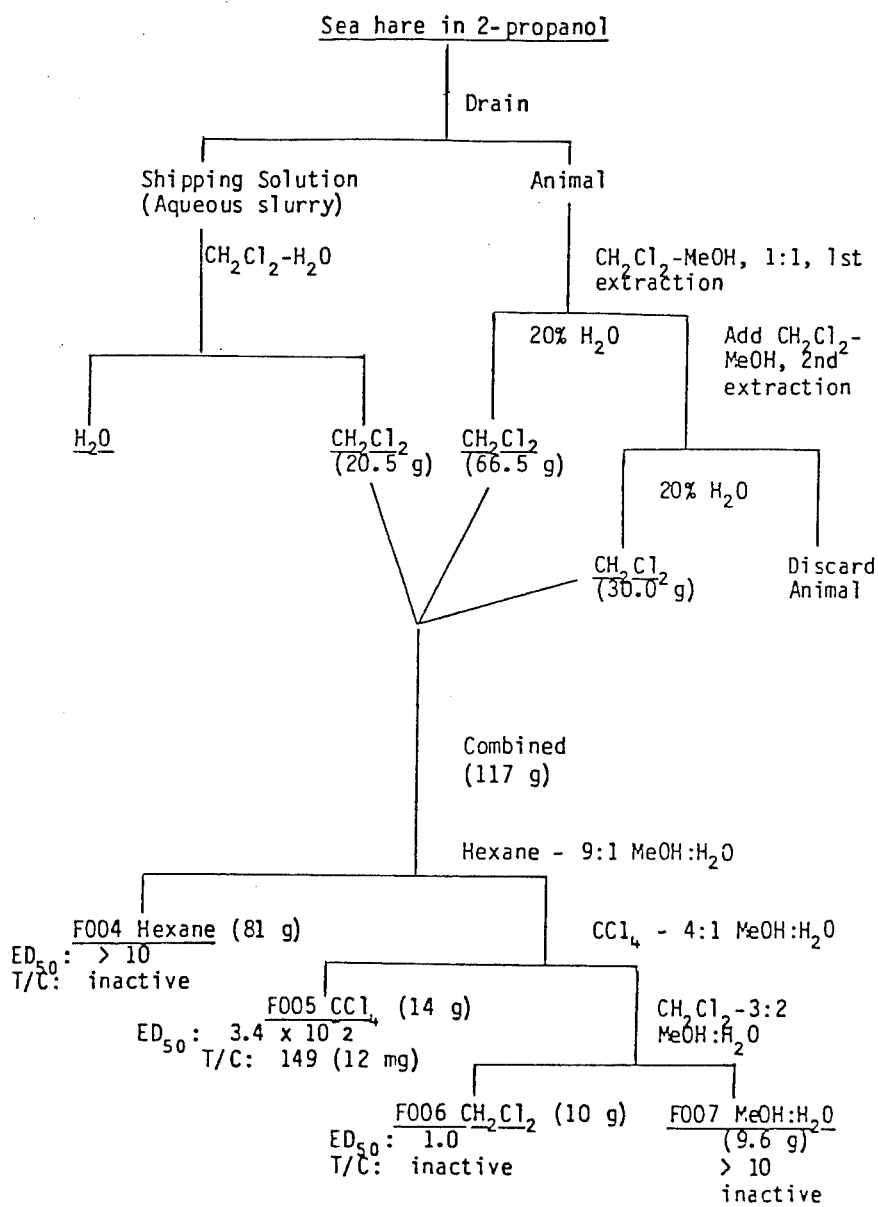
FIGURE II
Solvent Partitioning

DOLASTATINS A AND B CELL GROWTH INHIBITORY SUBSTANCES

DESCRIPTION

BRIEF SUMMARY OF THE INVENTION

Potent cell growth inhibitory substances designated dolastatins A and B extracted from the Indian Ocean sea hare Dolabella. Specifically, the novel compounds of the subject invention were isolated from the Philippine *Dolabella ecaudata*.

BACKGROUND OF THE INVENTION

The great Roman natural scientist Gaius Plinius Secundus (Pliny the Elder) in his comprehensive study of about 60 A.D. first described a most potent Indian Ocean sea hare of the genus Dolabella. [The Romans first designated Mollusca of the family Aplysidae as sea hares due to a similarity between the ears of a hare and the auriculate tentacles of these gastropods.] The potential of the Indian Ocean Dolabella with respect to modern medical problems is of recent origin. My pending U.S. patent application Ser. No. 297,473, filed on Aug. 28, 1981, discloses dolastatins 1 thru 3.

The dolastatins may correspond to the potent *D. auricularia* constituents recognized from ancient to fairly recent times [1969 Ph.D. dissertation of M. Watson, U. of Hawaii, "Some Aspects of the Pharmacology, Chemistry and Biology of the Midgut Gland Toxins of Some Hawaiian Sea Hares, especially *Dolabella auricularia* and *Aplysia pulmónica*," University Microfilms Inc., Ann Arbor, Mich.]. Since dolastatin 1 has been shown by the U.S. National Cancer Institute to cause an 88% life extension with the murine P388 lymphocytic leukemia, and a 30% curative response against the murine B16 melanoma at intraperitoneal doses of 11 μg/kg/day, it may represent the most active (lowest dose) presently known antineoplastic agent.

Financial assistance was provided by the National Cancer Institute (performed pursuant to contracts N01-CM-12308, 67048 and 97262 with the Division of Cancer Treatment, NCI, National Institutes of Health, DHW) and grant numbers CA-16049-01 through 06 awarded by the National Cancer Institute, DHW.

DETAILED DESCRIPTION OF THE INVENTION

The Organism

Taxonomy: Dolabella species belong to the family Aplysidae, the class Gastropoda and the phylum Mollusca. In a reference by H. Engel in "Zoologische Mededeelingen," Leiden, 24, 197–239 (1945), there are numerous color plates of specimens of Dolabella. Also in this reference is a listing of previously presumed different species of Dolabella which the author finds to be the same and identified as *Dolabella auricularia*. These species are: *Dolabella agassizi, D. andersonii, D. auricularia, D. callosa, D. dolabella, D. ecaudata, D. hasseltii, D. hemprichii, D. neira, D. peronii, D. rumphii, D. teremidi, D. tongana, D. truncata, D. variegata*, and *D. scapula*.

In appearance, the Dolabella used were olive green in color with a pear-shaped body and average length, 15–20 cm. The reference by H. Engel has detailed descriptions of Dolabella collected around the world.

The Dolabella collection site used for initial isolation of the dolastatins was on the eastern side of Mauritius in the Indian Ocean, approximate location, 21° S latitude, 56° E longitude, in 4–5 ft. deep water off the coast of the island.

Another site where Dolabella can be collected is near Negros Island in the Philippines, approximate location 9° N latitude, 123° E longitude. Extracts of Dolabella species from five separate collections all contained antineoplastic activity.

Isolation and Purification of Dolastatins

A variety of methods can be used to isolate and purify the dolastatins from samples of the sea hare, for example, solvent extraction, partition chromatography, silica gel chromatography, liquid-liquid distribution in a Craig apparatus, adsorption on resins, and crystallization from solvents.

The following examples describe preferred processes, but are not to be construed as limiting.

EXAMPLE 1

Isolation of Dalastatins A and B from the Philippine *Dolabella ecaudata*

*Dolabella ecaudata* was collected near Negros Island in the Philippines. Investigation of extracts of the sea hare from this location has resulted in the isolation of two new dalastatins (A and B). Now follows a disclosure of the isolation of dolastatins A (K095) and B (K094).

Twenty-five one-gallon cans of *Dolabella ecaudata* preserved in 2-propanol (shipping solution) were collected. The shipping solution was drained from the animal and concentrated to an aqueous slurry. The animal was ground (commercial meat grinder) and extracted with methylene chloride:methanol (1:1) at room temperature, in 15 gal. stainless steel containers for five days. To the decanted solution was added sufficient water (20% by volume) to provide two phases; the methylene chloride layer was removed and evaporated using a rotary evaporator. The upper layer was returned to the animal material, and sufficient methylene chloride-methanol was added to provide a single phase. A second extraction (at ambient temperature) for another five days, was performed. Again, water (20%) was added to the drained solution to give two phases. Each phase was dried (rotary evaporator). At this point, the animal residue was discarded. See FIG. I for an outline of the process.

The shipping solution, concentrated earlier to an aqueous suspension, was next partitioned with methylene chloride. The methylene chloride layer was evaporated to dryness (rotary evaporator) to give 20.5 g of extract which was combined with the first (66.5 g) and second (30.0 g) methylene chloride extracts from the two solvent extractions. The total extract (117.0 g) was carried through a solvent partition sequence.

The combined methylene chloride extracts were dissolved in 2-liters each of hexane and 9:1 methanol:water. The aqueous methanol was extracted five times with hexane (2-liters each time); the remaining 9:1 methanol:water solution was diluted to 4:1 methanol:water and extracted with carbon tetrachloride (2-liters, five times). Upon further dilution of the aqueous methanol to 3:2 methanol:water extraction was continued with methylene chloride (6 times 2-liters, each). Amounts of extract obtained were:

F004, hexane 81 g

F005, carbon tetrachloride, 14 g

F006, methylene chloride, 10 g
F007, aqueous methanol, 9.6 g.

The chromatographic separations performed beginning with the F005 and F006 fractions are outlined in FIG. II. Early separation steps involved extensive silica gel chromatography using dry column techniques and gradient elution with hexane-ethyl acetate to ethyl acetate-methanol-water. The active fractions were eluted with 98:2:0.5 ethyl acetate:methanol:water and mounted to 6.4 g (P388 ED$_{50}$ 0.14). After each chromatogram was complete the fractions were combined according to silica gel TLC comparisons (methylene chloride:methanol:water, 90:10:0.6 and ethyl acetate::ethyl alcohol, 9:1, developed twice) using UV and sulfuric acid (heated after spraying) as developing reagents, on precoated plates (Uniplate, Analtech, Inc.). The components visible by UV but not by sulfuric acid treatment were presumed to be the dolastatins. When HPLC techniques were used, the Altex preparative pump system with either a Magnun-9 ODS-2 column (methanol-water), or a Magnun-9 Partisil column (ethyl acetate-ethyl alcohol or methylene chloride-methanol-water) were employed. Fractions were combined according to UV absorbance as evidenced by a Gilson Holochrome monitoring unit.

Final separation of active (P388) fraction F091, 7.7 mg, was accomplished with preparative TLC on silica gel using half of a 20×20 cm plate (Whatman, Linear-K, 1000μ thickness). By this means, 3.5 mg of Dalastatin A (K095) and 1.5 mg of Dolastatin B (K094) were obtained.

Physical Data for Dolastatin A

| TLC, silica gel: | | |
|---|---|---|
| Rf | Solvent | Ratio |
| 0.53 | CH$_2$Cl$_2$/MeOH/H$_2$O | 90:10:0.8 |
| 0.49 | EtOAc/EtOH | 80:20 |
| 0.33 | EtOAc/EtOH | 90:10 |
| 0.15 | CH$_2$Cl$_2$/MeOH/H$_2$O + 5% HOAc | 90:10:0.8 |
| 0.68 | CH$_2$Cl$_2$/MeOH/H$_2$O − 5% Et$_2$NH | 90:10:0.8 |

| TLC, silica gel visualization: | |
|---|---|
| UV | ++ |
| H$_2$SO$_4$ | − |
| Anisaldehyde pale yellow | − |
| Ninhydrin | |
| Dragendorf orange, | before heating |
| | − after heating |
| Phosphomolibdic acid | + |

IR, KBr: 3430, 2964, 2938, 2874, 1731, 1663, 1630, 1446, 1379, 1308, 1252, 1192.

UV (MeOH): λ$_{max}$ 202, 204, 206 nm (E 8248), λ$_{max}$ 237 nm (E 3461).

Elemental Analysis: C, 63.34; H, 10.06; N, 12.10; S, 5.64.

Amino Acid Analysis:

| | Hydrolysis by: |
|---|---|
| H+ | OH− |
| Proline (16.61%) | Proline (11.63%) |
| Valine (4.99%) | Leucine (10.49%) |
| Leucine (8.63%) | no Valine was found |
| | + one unidentified compound |

MS: FAB: 837 (M+ +H), 552 (M+ +H-285), 498 (M+ +H-339), 340 (M+ +H-497), 297, 295, 288, 286, 258, 227, 215, 213, 207, 204, 199, 197, 100 (C$_6$H$_{14}$N+), 86, 72, 70, 45.

GCMS: Valine, Leucine and Proline identified.

NMR: 400 MH$_z$, CDCl$_3$, δ:

| | |
|---|---|
| 0.763 (3H, d, J=6.56H$_z$) | 3.732 (3H, S) |
| 0.908 (∼3H, d, J=7.16) | 3.775 (∼2H, dd, J=4.56, 14.68) |
| 0.926 (∼6H, d, J=7.64) | 3.877 (1H, broad t, J=?) |
| 1.019 (3H, d, J=6.44) | 4.618 (1H, t, J=∼6.10) |
| 1.057 (3H, d, J=6.84) | 4.699 (1H, S) |
| 1.232 (?, impurity, ∼1H, S) | 4.756 (1H, t, J=3.72) |
| 1.294 (1H, t, J=7.00, impurity ?) | 4.818 (1H, dd, J=2.46, 8.70) |
| 1.558 (7-8H, broad S, H$_2$O ?) | 5.115 (1Hd, J=11.04) |
| 1.845 (1H, td, J=11.76, 5.88) | 5.282 (2-3H, S) |
| 2.02-2.03 (∼3H, m) | 5.869 (1H, d, J=2.48) |
| 2.12-2.14 (∼2H, m) | ∼6.9 (1H, broad peak) |
| 2.05-2.3 (∼11H, m) | 712-7.21 (∼5H, m). |
| ∼2.35 (∼1H, m) | |
| 3.026 (1H, dd, J=3.32, 13.92) | |
| 3.157 (3H, S) | |
| 3.513 (1H, dd, J=14.12, 4.36) | |
| 3.581 (1H, dd, J=7.16, ?) | |

Physical Data for Dolastatin B

| TLC, silica gel: | | |
|---|---|---|
| Rf | Solvent | Ratio |
| 0.14 | CH$_2$Cl$_2$:MeOH:H$_2$O | 90:10:0.8 |
| ∼0. | EtOAc:EtOH | 80:20 |
| ∼0. | EtOAc:EtOH | 90:10 |
| 0.33 | CH$_2$Cl$_2$:MeOH:H$_2$O + 5% HOAc | 90:10:0.8 |
| 0.54 | CH$_2$Cl$_2$:MeOH:H$_2$O + 5% Et$_2$NH | 90:10:0.8 |

| Visualization on TLC (silica gel): | |
|---|---|
| UV | ++ |
| H$_2$SO$_4$ | − |
| Anisaldehyde | pale yellow |
| Ninhydrin | − |
| Dragendorf | orange before heating |
| | − after heating |
| Phosphomolibdic acid | + |

IR, KBr: 3433, 2963, 2925, 2873, 2852, 1729, 1668, 1661, 1630, 1567, 1445, 1383, 1306, 1253, 1190.

IU (MeOH): λ$_{max}$ 203, 206, nm (E 8332), λ$_{max}$ 238 nm (E 3525).

MS: FAB: 853 (M+ +H), (837), 823, (611), (583), 568, (552), 498, 356, 340, 326, 297, 296, 295, 288, 286, 281, (277?), 274, (243), 215, 213, 204 (197), (185?), 182, (154), 144, (131), (115?, 114, 112), 100, 98, (93?), 91, 86, 84, 83, (75?), 72, 70, 69, (61), (57?), 55, 45, 43, 41, 39, 31, 29, m/e 86 C$_5$H$_{12}$N, m/e 100 C$_6$H$_{14}$N.

| NMR: 400 MH$_z$, CDCl$_3$, δ | |
|---|---|
| 0.7715 (3H, d, J=6.28H$_z$) | 3.4728 (1H, S) |
| 0.8588 (3H, t, J=6.70H$_z$) | 3.527 (1H, dd, J=14.4 and 5.2H$_z$) |
| 0.9076 (3H, d, J=7.04H$_z$) | 3.602 (1H, m) |
| 0.9350 (3H?, d, J=6.36H$_z$) | 3.665 (?) |
| 0.9864 (3H, S?) | ∼3.72 (1H, m) |
| 1.0392 (3H, d, J=6.80H$_z$) | 3.733 (3H, S) |
| 1.0567 (3H, d, J=7.16H$_z$) | 3.800 (14, dd, J=?) |
| 1.295∼1.315 (∼1∼2H, m) | 3.89 (1H, broad t, J=?) |
| 1.405 (∼1H, S) impurity? | 4.62 (1H, broad t, J=?) |
| 1.79-1.90 (1∼2H) | 4.701 (1H, S) |
| 2.02-2.06 (22-26H) | 4.757 (1H, t or d) |
| 2.10-2.22 | 4.825 (1H, dd, J=8.8 and ? H$_z$) |
| 2.22-2.27 | 5.125 (1H, d, J=12H$_z$) |
| 2.32-2.40 | 5.281 (∼9H, S, ?, CH$_2$Cl$_2$?) |
| ∼2.55 (∼2H, broad peak) | 5.876 (1H, d, J=?) |
| 3.043 (1H, dd, J=14.4 and 3.3H$_z$) | 7.11-7.22 (4–5H, m) |
| 3.152 (3H, S) | ∼7.75 (1H, broad peak) |

Antineoplastic Activity of Dolastatins

| Compound | Mouse Tumor System | | | |
|---|---|---|---|---|
| | $B_{16}$ melanoma[a] | | $P_{388}$ leukemia[a] | |
| | optimal dose in µg/kg/ injection[b] | life span in percent of controls[c] | highest dose in µg/kg/ injection[b] | life span in percent of controls[c] |
| Dolastatin A | | | 150 | 126 |

[a]tumors were inoculated intraperitoneally (i.p.)
[b]compounds were administered i.p. everyday for 9 days starting on the first day after tumor inoculation.
[c]Calculated from median survival times; Nos. in parentheses = No. of cures/total No. of mice in group. Cured mice survive for at least 60 days.

In an in vitro test against the P388 lymphocytic leukemia cell line, dolastatin A and dolastatin B gave the following results:

Dolastatin A P388 $ED_{50}$, $1.8 \times 10^{-8}$

Dolastatin B P388 $ED_{50}$, $1.0 \times 10^{-4}$.

The P388 in vitro test is run in the same manner as the L1210 in vitro test described in G. L. Neil et al., Cancer Treatment Reports 63, 1971-1978 (1979). The P388 in vivo test is also described in this publication.

Other neoplastic diseases may be amenable to therapy with dolastatin A and dolastatin B.

The dosage administered will be dependent upon the identity of the neoplastic disease, the type of host involved, its age, health, weight, kind of concurrent treatment, if any, frequency of treatment and therapeutic ratio.

Illustratively, dosage levels of the administered active ingredients can be: intravenous, 0.1 to about 200 µg/kg; intraperitoneal, 1 to about 1000 µg/kg; subcutaneous, 1 to about 1000 µg/kg; intramuscular, 1 to about 1000 µg/kg; orally, 0.01 to about 10 mg/kg; intranasal instillation, 0.01 to about 10 mg/kg; and aerosol, 0.01 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs, and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral or anti-neoplastic agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

COMPOSITION EXAMPLE 1

Hard-Gelatin Capsules

One thousand two-piece hard gelatin capsules for oral use, each capsule containing 10 mg of a dolastatin, are prepared from the following types and amounts of ingredients:

| a dolastatin, micronized | 10 gm |
|---|---|
| Lactose | 190 gm |
| Corn Starch | 20 gm |
| Talc | 20 gm |
| Magnesium stearate | 2 gm |

The dolastatin finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a dolastatin in 5, 25 and 50 mg amounts by substituting 5 gm, 25 gm and 50 gm of a dolastatin for the 100 gm used above.

COMPOSITION EXAMPLE 2

Soft Gelatin Capsules

One-piece soft gelatin capsules for oral use, each containing 250 mg of a dolastatin (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION EXAMPLE 3

Tablets

One thousand tablets, each containing 50 mg of a dolastatin are prepared from the following types and amounts of ingredients:

| A dolastatin, micronized | 50 gm |
|---|---|
| Lactose | 525 gm |
| Corn starch | 50 gm |
| Magnesium stearate | 4 gm |
| Light liquid petrolatum | 5 gm |

The dolastatin finely divided by means of an air micronizer, is added to the other ingredients and then thoroughly mixed an slugged. The slugs are broken down by forcing through a Number Sixteen screen. The resulting granules are then compressed into tablets, each tablet containing 50 mg of the dolastatin.

The foregoing tablets are useful for treating a neoplastic disease by the oral administration of one or two tablets one to four times a day.

Using the procedure above, tablets are similarly prepared containing a dolastatin in 25 mg and 10 mg amounts by substituting 25 gm and 1 gm of a dolastatin for the 50 gm used above.

COMPOSITION EXAMPLE 4

Oral Suspension

One thousand ml of an aqueous suspension for oral use, containing in each teaspoonful (5 ml) dose, 50 mg of a dolastatin, is prepared from the following types and amounts of ingredients:

| A dolastatin, micronized | 10 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The dolastatin, finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION EXAMPLE 5

A sterile aqueous suspension for parenteral injection, containing in 1 ml 300 mg of a dolastatin for treating a neoplastic disease, is prepared from the following types and amounts of ingredients:

| | |
|---|---|
| A dolastatin, micronized | 30 gm |
| Polysorbate 80 | 5 gm |
| Methylparaben | 2.5 gm |
| Propylparaben | 0.17 gm |
| Water for injection, q.s. 1000 ml. | |

All the ingredients, except the dolastatin, are dissolved in the water and the solution sterilized by filtration. To the sterile solution is added the sterilized dolastatin, finely divided by means of an air micronizer, and the final suspension is filled into sterile vials and the vials sealed.

The composition so prepared is useful for treating a neoplastic disease at a dose of 1 milliliter (1 M) three times a day.

COMPOSITION EXAMPLE 6

Suppository, Rectal and Vaginal

One thousand suppositories, each weighing 2.5 gm and containing 15 mg of a dolastatin are prepared from the following types and amounts of ingredients:

| | |
|---|---|
| A dolastatin, micronized | 15 gm |
| Propylene glycol | 150 gm |
| Polyethylene glycol #4000, q.s. | 2,500 gm |

The dolastatin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION EXAMPLE 7

Intranasal Suspension

One thousand ml of a sterile aqueous suspension for intranasal instillation, containing in each ml 15 mg of a dolastatin, is prepared from the following types and amounts of ingredients:

| | |
|---|---|
| A dolastatin, micronized | 15 gm |
| Polysorbate 80 | 5 gm |
| Methylparaben | 2.5 gm |
| Propylparaben | 0.17 gm |
| Deionized water, q.s. 1000 ml. | |

All the ingredients, except the dolastatin, are dissolved in the water and the solution sterilized by filtration. To the sterile solution is added the sterilized dolastatin, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present, as shown in Examples 12-14 in the undiluted pure form for use locally about the cutis, intranasally, pharyngolaryngeally, bronchially, broncholially or orally.

COMPOSITION EXAMPLE 8

Powder

Five grams of a dolastatin in bulk form is finely divided by means of an air micronizer. The micronized powder is placed in a shaker-type container.

The foregoing composition is useful for treating a neoplastic disease, at localized sites by applying the powder one to four times per day.

COMPOSITION EXAMPLE 9

Oral Powder

One hundred grams of a dolastatin in bulk form is finely divided by means of an air micronizer. The micronized powder is divided into individual doses of 25 mg and packaged.

The foregoing powders are useful for treating a neoplastic disease, by the oral administration of one or two powders suspended in a glass of water, one to four times per day.

COMPOSITION EXAMPLE 10

Insufflation

One hundred grams of a dolastatin in bulk form is finely divided by means of an air micronizer.

The foregoing composition is useful for treating a neoplastic disease, by the inhalation of 3 to 8 mg one to four times per day.

COMPOSITION EXAMPLE 11

Hard Gelatin Capsules

One hundred two-piece hard gelatin capsules for oral use, each capsule containing 10 mg of a dolastatin.

The dolastatin is finely divided by means of an air micronizer and encapsulated in the usual manner.

The foregoing capsules are useful for treating a neoplastic disease, by the oral administration of one or two capsules one to four times a day.

Using the procedure above, capsules are similarly prepared containing dolastatin in 5, 25 and 50 mg amounts by substituting 5 gm, 25 gm and 50 gm of a dolastatin for the 10 gm used above.

I claim:

1. Cell growth inhibitory substance designated dolastatin A which has the following characteristics:

Physical Data for Dolastatin A

| TLC, silica gel: | | |
|---|---|---|
| Rf | Solvent | Ratio |
| 0.53 | $CH_2Cl_2$/MeOH/$H_2O$ | 90:10:0.8 |
| 0.49 | EtOAc/EtOH | 80:20 |
| 0.33 | EtOAc/EtOH | 90:10 |
| 0.15 | $CH_2Cl_2$/MeOH/$H_2O$ + 5% HOAc | 90:10:0.8 |
| 0.68 | $CH_2Cl_2$/MeOH/$H_2O$ − 5% $Et_2NH$ | 90:10:0.8 |

| TLC, silica gel visualization: | |
|---|---|
| UV | ++ |
| $H_2SO_4$ | − |
| Anisaldehyde pale yellow | − |
| Ninhydrin | |

| -continued | |
|---|---|
| Dragendorf orange, | before heating |
| | − after heating |
| Phosphomolibdic acid | + |

IR, KBr: 3430, 2964, 2938, 2874, 1731, 1663, 1630, 1446, 1379, 1308, 1252, 1192,
UV (MeOH): $\lambda_{max}$ 202, 204, 206 nm (E 8248), $\lambda_{max}$ 237 nm (E 3461).
Elemental Analysis: C, 63.34; H, 10.06; N, 12.10; S, 5.64; Amino Acid Analysis:

| Hydrolysis by: | |
|---|---|
| H$^+$ | OH$^-$ |
| Proline (16.61%) | Proline (11.63%) |
| Valine (4.99%) | Leucine (10.49%) |
| Leucine (8.63%) | no Valine was found |
| | + one unidentified compound |

MS: FAB: 837 (M$^+$+H), 552 (M$^+$+H-285), 498 (M$^+$+H-339), 340 (M$^+$+H-497), 297, 295, 288, 286, 258, 227, 215, 213, 207, 204, 199, 197, 100 (C$_6$H$_{14}$N$^+$), 86, 72, 70, 45;
GCMS: Valine, Leucine and Proline identified;
NMR: 400 MHz, CDCl$_3$, δ:

| | |
|---|---|
| 0.763 (3H, d, J=6.56H$_z$) | 3.732 (3H, S) |
| 0.908 (~3H, d, J=7.16) | 3.775 (~2H, dd, J=4.56, 14.68) |
| 0.926 (~6H, d, J=7.64) | 3.877 (1H, broad t, J=?) |
| 1.019 (3H, d, J=6.44) | 4.618 (1H, t, J=~6.10) |
| 1.057 (3H, d, J=6.84) | 4.699 (1H, S) |
| 1.232 (?, impurity, ~1H, S) | 4.756 (1H, t, J=3.72) |
| 1.294 (1H, t, J=7.00, impurity?) | 4.818 (1H, dd, J=2.46, 8.70) |
| 1.558 (7-8H, broad S, H$_2$O?) | 5.115 (1Hd, J=11.04) |
| 1.845 (1H, td, J=11.76, 5.88) | 5.282 (2-3H, S) |
| 2.02-2.03 (~3H, m) | 5.869 (1H, d, J=2.48) |
| 2.12-2.14 (~2H, m | ~5.9 (1H, broad peak) |
| 2.05-2.3 (~11H, m) | 712-7.21 (~5H, m) |
| ~2.35 (~1H, m) | |
| 3.026 (1H, dd, J=3.32, 13.92) | |
| 3.157 (3H, S) | |
| 3.513 (1H, dd, J=14.12, 4.36 | |
| 3.581 (1H, dd, J=7.16, ?). | |

2. Cell growth inhibitory substance designated dolastatin B which has the following characteristics:

Physical Data for Dolastatin B

| TLC, silica gel: | | |
|---|---|---|
| Rf | Solvent | Ratio |
| 0.14 | CH$_2$Cl$_2$:MeOH:H$_2$O | 90:10:0.8 |
| ~0. | EtOAc:EtOH | 80:20 |
| ~0. | EtOAc:EtOH | 90:10 |
| 0.33 | CH$_2$Cl$_2$:MeOH:H$_2$O + 5% HOAc | 90:10:0.8 |
| 0.54 | CH$_2$Cl$_2$:MeOH:H$_2$O + 5% Et$_2$NH | 90:10:0.8 |
| Visualization on TLC (silica gel): | | |
| UV | ++ | |
| H$_2$SO$_4$ | − | |

| -continued | |
|---|---|
| Anisaldehyde | pale yellow |
| Ninhydrin | − |
| Dragendorf | orange before heating |
| | − after heating |
| Phosphomolibdic acid | + |

IR, KBr: 3433, 2963, 2925, 2873, 2852, 1729, 1668, 1661, 1630, 1567, 1445, 1383, 1306, 1253, 1190,
UV (MeOH): $\lambda_{max}$ 203, 206, nm (E 8332), $\lambda_{max}$ 238 nm (E 3525),
MS: FAB: 853 (M$^+$+H, (837), 823, (611), (583), 568, (552), 498, 356, 340, 326, 297, 296, 295, 288, 286, 281, (277?), 274, (243), 215, 213, 204 (197), (185?), 182, (154), 144, (131), (115?, 114, 112), 100, 98, (93!), 91, 86, 84, 83, (75?), 72, 70, 69, (61), (57?), 55, 45, 43, 41, 39, 31, 29, m/e 86 C$_5$H$_{12}$N, m/e 100 C$_6$H$_{14}$N,
NMR: 400 MHz, CDCl$_3$, δ:

| | |
|---|---|
| 0.7715 (3H, d, J=6.28H$_z$) | 3.4728 (1H, S) |
| 0.8588 (3H, t, J=6.70H$_z$) | 3.527 (1H, dd, J=14.4 and 5.2H$_z$) |
| 0.9076 (3H, d, J=7.04H$_z$) | 3.602 (1H, m) |
| 0.9350 (3H?, d, J=6.36H$_z$) | 3.665 (?) |
| 0.9864 (3H, S?) | ~3.72 (1H, m) |
| 1.0392 (3H, d, J=6.80H$_z$) | 3.733 (3H, S) |
| 1.0567 (3H, d, J=7.16H$_z$) | 3.800 (14, dd, J=?) |
| 1.295~1.315 (~1~2H, m) | 3.89 (1H, broad t, J=?) |
| 1.405 (~1H, S) impurity? | 4.62 (1H, broad t, J=?) |
| 1.79-1.90 (1~2H) | 4.701 (1H, S) |
| 2.02-2.06 (22-26H) | 4.757 (1H, t or d) |
| 2.10-2.22 | 4.825 (1H, dd, J=8.8 and ? H$_z$) |
| 2.22-2.27 | 5.125 (1H, d, J=12H$_z$) |
| 2.32-2.40 | 5.281 (~9H, S, ?, CH$_2$Cl$_2$?) |
| ~2.55 (~2H, broad peak) | 5.876 (1H, d, J=?) |
| 3.043 (1H, dd, J=14.4 and 3.3H$_z$) | 7.11-7.22 (4~5H, m) |
| 3.152 (3H, S) | ~7.75 (1H, broad peak) |

3. A process for treating a host having P388 leukemia which comprises the administration of an effective amount of dolastatin A to said host.

4. A process for treating a host having P388 leukemia which comprises the administration of an effective amount of dolastatin B to said host.

5. A process for preparing dolastatins active against P388 leukemia which comprises:
(a) extracting a ground preparation of the Indian Ocean sea hare Dolabella wth methylene chloride:-methanol (1:1) to obtain an extract;
(b) subjecting said extract to solvent partitioning to obtain an extract showing activity against P388 leukemia;
(c) chromatographing said active extract and isolating the fractions active against P388 leukemia; and,
(d) rechromatographing said active fraction to obtain further fractions active against P388 leukemia.

6. A process for preparing dolastatin A which comprises chromatographing the final active fractions obtained in claim 5 on silica gel.

7. A process for preparing dolastatin B which comprises chromatographing the final active fractions obtained in claim 5 on silica gel.

* * * * *

UNITED STATES PATENT OFFICE
CERTIFICATE OF CORRECTION

Patent No. 4,486,414      Dated 4 December 1984

Inventor(s) George R. Pettit

It is certified that error appears in the above-identified patent and that said Letters Patent are hereby corrected as shown below:
Column 3, line 10, "mounted to " should read -- amounted to --.
Column 4, line 43, "IU (MeOH):" should read -- UV (MeOH): --.
Column 11, line 39, "~5.9 (1H," should read -- ~6.9 (1H, --.
Column 12, line 16, "(93!)," should read -- (93?) --.

Signed and Sealed this

Twenty-ninth Day of October 1985

[SEAL]

Attest:

DONALD J. QUIGG

Attesting Officer      Commissioner of Patents and Trademarks—Designate